US011840507B2

(12) United States Patent
Mayerhoeffer et al.

(10) Patent No.: US 11,840,507 B2
(45) Date of Patent: Dec. 12, 2023

(54) PROCESS FOR THE PREPARATION OF PHENYL KETONES

(71) Applicant: ARXADA AG, Visp (CH)

(72) Inventors: Ulrich Mayerhoeffer, Visp (CH); Eva Kirchner, Visp (CH); Fabian Meemken, Visp (CH); Christophe Girard, Visp (CH); Kai Lechner, Visp (CH); Emilia Paunescu, Visp (CH)

(73) Assignee: ARXADA AG, Visp (CH)

( * ) Notice: Subject to any disclaimer, the term of this patent is extended or adjusted under 35 U.S.C. 154(b) by 0 days.

(21) Appl. No.: 18/006,588

(22) PCT Filed: Aug. 16, 2021

(86) PCT No.: PCT/EP2021/072758
§ 371 (c)(1),
(2) Date: Jan. 24, 2023

(87) PCT Pub. No.: WO2022/038098
PCT Pub. Date: Feb. 24, 2022

(65) Prior Publication Data
US 2023/0242469 A1 Aug. 3, 2023

(30) Foreign Application Priority Data

Aug. 19, 2020 (EP) ..................... 20191749
Apr. 29, 2021 (EP) ..................... 21171158

(51) Int. Cl.
C07C 45/64 (2006.01)

(52) U.S. Cl.
CPC .......... *C07C 45/64* (2013.01); *C07C 2601/16* (2017.05)

(58) Field of Classification Search
CPC ............. C07C 45/64; C07C 2601/16
See application file for complete search history.

(56) References Cited

U.S. PATENT DOCUMENTS

| 9,783,476 B2 | 10/2017 | Nakatani et al. |
| 10,358,426 B2 | 7/2019 | Dietz et al. |

FOREIGN PATENT DOCUMENTS

| CN | 105440022 | 3/2016 |
| CN | 109824493 | 5/2019 |
| DE | 10027654 | 12/2001 |
| JP | 2019069922 | 5/2019 |
| JP | 2020169310 | 10/2020 |
| WO | WO2004050654 | 6/2004 |
| WO | WO2015091045 | 6/2015 |
| WO | WO2016202807 | 12/2016 |

OTHER PUBLICATIONS

Database Caplus Chemical Abstracts Service, Columbus, Ohio, US; Rahman, M. T.; Nur, H. P.: "The reaction of arylmagnesium halides with succinic anhydride", 1 page, Nov. 23, 2021.
International Search Report and Written Opinion for PCT/EP2021/072758 dated Apr. 14, 2022, 17 pages.
Nakatani et al. Organic Process Research & Development, "Preparation of Trifluoromethylphenyl Magnesium Halides in the Presence of LiCl and Synthesis of 2'-Trifluoromethyl-Aromatic Ketones," 2016. vol. 20, p. 1633-1636.
Larock, "Comprehensive Organic Transformation, A Guide to Functional Group Preparations", $2^{nd}$ Edition, 1999, p. 894-895.
Ouali et al., "Grignard reagents and Copper", De Gruyter, Physical Sciences Reviews, 2016, 17 pages.
Smith et al., "March's Advanced Organic Chemistry, Reactions, Mechanisms, and Structure", $5^{th}$ Edition, 2001, p. 862-863.
Rahman et al., "The Reaction of Arylmagnesium Halides with Succinic Anhydride", J. Indian Chem. Soc., 1994, vol. 71, pp. 469-474.

*Primary Examiner* — Sikarl A Witherspoon
(74) *Attorney, Agent, or Firm* — Dority & Manning, P.A.

(57) ABSTRACT

The present invention relates to a process for the preparation of phenyl ketones and the preparation of phenoxyphenyl derivatives.

22 Claims, No Drawings

PROCESS FOR THE PREPARATION OF PHENYL KETONES

RELATED APPLICATIONS

The present application is the National Stage entry of International Patent Application No. PCT/EP2021/072758 filed on Aug. 16, 2021, which is based on and claims priority to European Patent application No. 20191749.9, filed on Aug. 19, 2020, and European Patent application No. 21171158.5, filed on Apr. 29, 2021, each of which is incorporated herein by reference.

TECHNICAL FIELD

The present invention relates to a process for the preparation of phenyl ketones and the preparation of phenoxyphenyl derivatives.

TECHNOLOGICAL BACKGROUND

Phenyl ketones and phenoxyphenyl derivatives prepared therefrom are valuable compounds and intermediates in the synthesis of several further compounds used for example as pesticides such as fungicides.

WO 2013/007767 A1 discloses the preparation of 2-[2-chloro-4-(4-chlorophenoxy)-phenyl]-1-[1,2,4]triazol-1-yl-ethanol that can be synthesised via phenyl ketone intermediate compounds.

WO 2014/108286 A1 discloses the synthesis of phenoxyphenyl derivatives via phenyl ketones.

The known processes however suffer from drawbacks like difficult and laborious work-up and purification steps, lower production rates or the formation of undesired side products. Furthermore, the known processes use metal catalysts, such as Cu(I) salts or Li salts for selectivity and rate increase. The use of metal catalysts however is critical inter alia in view of environmental aspects.

Hence, there is an ongoing need for optimized processes for the synthesis of phenyl ketones that are valuable intermediates for the preparation of phenoxyphenyl derivatives.

An object of the present invention is to provide an excellent process for the synthesis of phenyl ketones according to formula (II). A further object of the present invention is to provide an excellent process for the synthesis of phenoxyphenyl derivatives according to formula (I) via the inventive process for preparing phenyl ketones according to formula (II), which serve as intermediates in the synthesis of said phenoxyphenyl derivatives according to formula (I).

SUMMARY OF THE INVENTION

In one aspect, the present invention provides a process for the preparation of a compound of formula (II)

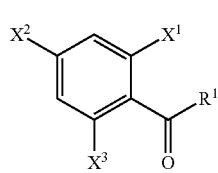

wherein
$X^1$ is selected from H, F, $CH_3$, $CH_2F$, $CHF_2$, and $CF_3$,
$X^2$ is H, F, Cl, or $NO_2$,
$X^3$ is selected from H, F, $CH_3$, $CH_2F$, $CHF_2$, and $CF_3$, and
$R^1$ is selected from linear or branched $C_{1-12}$ alkyl, linear or branched $C_{1-12}$ fluoroalkyl, $C_{3-8}$ cycloalkyl, linear or branched $C_{2-12}$ hydroxyalkyl, linear or branched $C_{1-12}$ carboxyalkly, phenyl and optionally substituted carboxy phenyl;
the process comprising
(i) reacting a compound of formula (III)

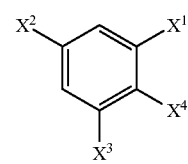

wherein $X^4$ is Br or Cl
with
a compound of formula (IV) $R^2$—Mg-Hal (IV) or Mg, and
a compound of formula (V) $R^{1a}$—C(=O)OC(=O)—$R^{1a}$ (V), a cyclic anhydride or a lactone, wherein
$R^{1a}$ is selected from linear or branched $C_{1-12}$ alkyl, linear or branched $C_{1-12}$ fluoroalkyl, $C_{3-8}$ cycloalkyl, and phenyl,
Hal is halogen, and
$R^2$ is selected from a linear or branched $C_{1-6}$ alkyl, $C_{3-6}$ cycloalkyl, and phenyl.

In a further aspect, the present invention provides a process for the preparation of a compound of formula (I)

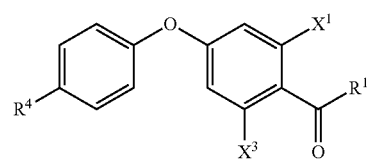

wherein
$X^1$ is selected from H, F, $CH_3$, $CH_2F$, $CHF_2$, and $CF_3$,
$X^3$ is selected from H, F, $CH_3$, $CH_2F$, $CHF_2$, and $CF_3$,
$R^1$ is selected from linear or branched $C_{1-12}$ alkyl, $C_{1-12}$ fluoroalkyl, $C_{3-8}$ cycloalkyl, linear or branched $C_{2-12}$ hydroxyalkyl, linear or branched $C_{1-12}$ carboxyalkly, phenyl and optionally substituted carboxy phenyl, and
$R^4$ is halogen;
the process comprising
(i) the process according to the present invention for obtaining a compound of formula (II) as defined herein with the proviso that in the compound of formula (II) $X^2$ is F, Cl, or $NO_2$, and
(ii) reacting the compound of formula (II) obtained in step (i) with a compound of formula (VI)

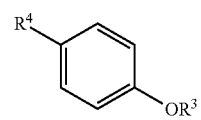

wherein $R^3$ is hydrogen or an alkali metal cation.

DETAILED DESCRIPTION OF THE INVENTION

In the following, the invention will be explained in more detail.

According to the present invention, the term "linear or branched $C_{1-12}$ alkyl" refers to a straight-chained or branched saturated hydrocarbon group having 1 to 12 carbon atoms, such as 1, 2, 3, 4, 5, 6, 7, 8, 9, 10, 11 or 12 carbon atoms. Likewise, the term "linear or branched $C_{1-6}$ alkyl" refers to a straight-chained or branched saturated hydrocarbon group having 1 to 6 carbon atoms (i.e. 1, 2, 3, 4, 5, or 6 carbon atoms) including methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethyl propyl, 1,2,2-trimethylpropyl, 1-ethyl-1-methylpropyl and 1-ethyl-2-methylpropyl.

According to the present invention, the term "linear or branched $C_{1-4}$ alkyl" refers to a straight-chained or branched saturated hydrocarbon group having 1 to 4 carbon atoms including methyl, ethyl, n-propyl, iso-propyl, n-butyl, iso-butyl, sec-butyl, and tert-butyl.

According to the present invention, the term "linear or branched $C_{1-12}$ fluoroalkyl" refers a straight-chained or branched saturated hydrocarbon group having 1 to 12 carbon atoms as defined above, wherein at least one hydrogen atom is replaced by a fluoro atom. Likewise, the term "linear or branched $C_{1-6}$ fluoroalkyl" refers to a straight-chained or branched saturated hydrocarbon group having 1 to 6 carbon atoms as defined above, wherein at least one hydrogen atom is replaced by a fluoro atom, including fluoromethyl, difluoromethyl, trifluoromethyl, 1-fluoroethyl, 2-fluoroethyl, 2,2-difluoroethyl, 2,2,2-trifluoroethyl, pentafluoroethyl, 3,3,3-trifluorpropyl, 4,4,4,-trifluorobutyl, 5,5,5,-trifluoropentyl, and 6,6,6-trifluorohexyl. Also included are perfluorinated alkyl groups such as linear or branched $C_{1-12}$ perfluoroalkyl and linear or branched $C_{1-6}$ perfluoroalkyl.

According to the present invention, the term "$C_{3-8}$ cycloalkyl" refers to monocyclic saturated hydrocarbon radicals having 3 to 8 carbon ring members including cyclopropyl, cyclobutyl, cyclopentyl, cyclohexyl, cycloheptyl, and cyclooctyl. Likewise, the term "$C_{3-6}$ cycloalkyl" refers to monocyclic saturated hydrocarbon radicals having 3 to 6 carbon ring members including cyclopropyl, cyclobutyl, cyclopentyl, and cyclohexyl.

According to the present invention, the term "linear or branched $C_{2-12}$ hydroxyalkyl" refers a straight-chained or branched saturated hydrocarbon group having 2 to 12 carbon atoms as defined above, wherein at least one hydrogen atom is replaced by a hydroxy group. Likewise, the term "linear or branched $C_{2-6}$ hydroxyalkyl" refers to a straight-chained or branched saturated hydrocarbon group having 2 to 6 carbon atoms as defined above, wherein at least one hydrogen atom is replaced by a hydroxy group, including 1-hydroxyethyl, 2-hydroxyethyl, 1-hydroxypropyl, 2-hydroxypropyl, 3-hydroxypropyl, 2-hydroxyisopropy, 1-hydroxybutyl, 2-hydroxybutyl, 3-hydroxybutyl, 4-hydroxybutyl, 1-hydroxypentyl, 2-hydroxypentyl, 3-hydroxypentyl, 4-hydroxypentyl, 5-hydroxypentyl, 1-hydroxyhexyl, 2-hydroxyhexyl, 3-hydroxyhexyl, 4-hydroxyhexyl, 5-hydroxyhexyl, and 6-hydroxyhexyl.

According to the present invention, the term "linear or branched $C_{1-12}$ carboxyalkly" refers a straight-chained or branched saturated hydrocarbon group having 1 to 12 carbon atoms as defined above, wherein at least one hydrogen atom is replaced by a carboxy group. Likewise, the term "linear or branched $C_{1-6}$ carboxyalkly" refers to a straight-chained or branched saturated hydrocarbon group having 1 to 6 carbon atoms as defined above, wherein at least one hydrogen atom is replaced by a carboxy group, including carboxymethyl, 1-carboxyethyl, 2-carboxyethyl, 1-methyl-2-carboxyethyl, 1-carboxypropyl, 2-carboxypropyl, 3-carboxypropyl, 1-methyl-2-carboxypropyl, 1-methyl-3-carboxypropyl, 1,1-dimethyl-2-carboxypropyl, 1,1-dimethyl-3-carboxypropyl, 1,2-dimethyl-3-carboxypropyl, 2,2-dimethyl-3-carboxypropyl, 1-carboxybutyl, 2-carboxybutyl, 3-carboxybutyl, 4-carboxybutyl, 1-methyl-4-carboxybutyl, 2-methyl-4-carboxybutyl, 3-methyl-4-carboxybutyl, 1,1-dimethyl-4-carboxybutyl, 1,2-dimethyl-4-carboxybutyl, 1,3-dimethyl-4-carboxybutyl, 2,2-dimethyl-4-carboxybutyl, 2,3-dimethyl-4-carboxybutyl, 3,3-dimethyl-4-carboxybutyl, 5-carboxypentyl, and 6-carboxyhexyl.

It is to be understood that the linear or branched $C_{1-12}$ alkyl, linear or branched $C_{1-6}$ alkyl, linear or branched $C_{1-4}$ alkyl, linear or branched $C_{1-12}$ fluoroalkyl, linear or branched $C_{1-6}$ fluoroalkyl, $C_{3-8}$ cycloalkyl, linear or branched $C_{2-12}$ hydroxyalkyl, linear or branched $C_{2-6}$ hydroxyalkyl, linear or branched $C_{1-12}$ carboxyalkly, linear or branched $C_{1-6}$ carboxyalkly, and phenyl may optionally be further substituted. Exemplary substituents include hydroxy, linear or branched $C_{1-12}$ alkyl, $C_{3-8}$ cycloalkyl, a carboxy group, halogen, and phenyl.

According to the present invention, the term "Hal" or "halogen" refers to fluorine, chlorine, bromine and iodine.

The meanings and preferred meanings described herein for substituents $R^1$, $R^{1a}$, $R^2$, $R^3$, $R^4$, Hal, $X^1$, $X^2$, $X^3$ and $X^4$ apply to all compounds and the precursors of the compounds in any of the process steps detailed herein.

As outlined above, subject of the present invention is a process for the preparation of a compound of formula (II)

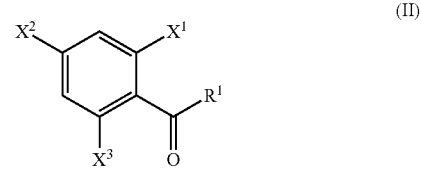

(II)

wherein $X^1$ is selected from H, F, $CH_3$, $CH_2F$, $CHF_2$, and $CF_3$, $X^2$ is H, F, Cl, or $NO_2$, $X^3$ is selected from H, F, $CH_3$, $CH_2F$, $CHF_2$, and $CF_3$, and $R^1$ is selected from linear or branched $C_{1-12}$ alkyl, linear or branched $C_{1-12}$ fluoroalkyl, $C_{3-8}$ cycloalkyl, linear or branched $C_{2-12}$ hydroxyalkyl, linear or branched $C_{1-12}$ carboxyalkly, phenyl and optionally substituted carboxy phenyl;

the process comprising
(i) reacting a compound of formula (III)

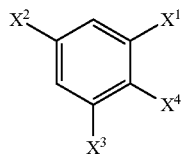

wherein X⁴ is Br or Cl
with
a compound of formula (IV) $R^2$—Mg-Hal (IV) or Mg, and
a compound of formula (V) $R^{1a}$—C(=O)OC(=O)—$R^{1a}$ (V), a cyclic anhydride or a lactone, wherein
$R^{1a}$ is selected from linear or branched $C_{1-12}$ alkyl, linear or branched $C_{1-12}$ fluoroalkyl, $C_{3-8}$ cycloalkyl, and phenyl,
Hal is halogen, and
$R^2$ is selected from a linear or branched $C_{1-6}$ alkyl, $C_{3-6}$ cycloalkyl, and phenyl.

In one embodiment, the present invention provides a process for the preparation of a compound of formula (IIa)

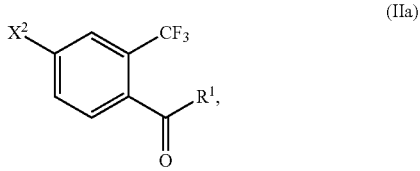

wherein
$X^2$ is H, F, Cl, or $NO_2$, preferably $X^2$ is F, Cl, or $NO_2$, and
$R^1$ is a linear or branched $C_{1-6}$ alkyl or $C_{3-8}$ cycloalkyl;
the process comprising
(i) reacting a compound of formula (IIIa)

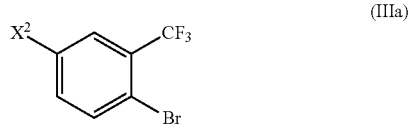

with
a compound of formula (IV) $R^2$—Mg-Hal (IV) or Mg, and
a compound of formula (V) Ria-C(=O)OC(=O)—$R^{1a}$ (V),
wherein
$R^{1a}$ is a linear or branched $C_{1-6}$ alkyl or $C_{3-8}$ cycloalkyl,
Hal is halogen, and
$R^2$ is selected from a linear or branched $C_{1-6}$ alkyl, $C_{3-6}$ cycloalkyl, and phenyl.

In one embodiment, the compound of formula (II) is the compound of formula (IIa) and the compound of formula (III) is the compound of formula (IIIa).

The inventors surprisingly found that the process according to the present invention for the preparation of a compound of formula (II), such as a compound of formula (IIa), provides a high throughput and a significantly reduced work-up process. Moreover, the inventors surprisingly found that with the process according to the present invention for the preparation of a compound of formula (II), such as a compound of formula (IIa), no catalyst, particularly no metal catalyst such as a copper catalyst like a Cu(I)-catalyst, or lithium salts as catalyst is needed. Furthermore, less side products are formed during the production of the compound of formula (II), such as a compound of formula (IIa). Furthermore, the process according to the present invention for the preparation of a compound of formula (II), such as a compound of formula (IIa), is more cost-efficient compared to the known production methods.

In one embodiment, no catalyst, preferably no metal catalyst, is present in reaction step (i). Thus, in said embodiment, the compound of formula (III), such as a compound of formula (IIIa), is reacted with the Grignard reagent $R^2$—Mg-Hal (IV) and the anhydride Ria-C(=O)OC(=O)—$R^{1a}$ (V), the cyclic anhydride or the lactone in the absence of a catalyst. In one embodiment no copper catalyst and/or lithium salt catalyst is present in reaction step (i). Preferably, no copper catalyst such as a Cu(I) or Cu(II) catalyst is present in reaction step (i), more preferably no Cu(I) catalyst is present in reaction step (i), and most preferably no CuCl catalyst is present in reaction step (i). Catalysts, such as Cu(I) or Cu(II) catalysts, like CuCl or $CuCl_2$, necessitate a solid dosage in the process for preparing a compound of formula (II), such as a compound of formula (IIa), which may be undesirable. Furthermore, Cu(I) is a biocide which must be removed in a waste water treatment plant prior to release.

$X^2$ in the occurrences herein is selected from H, F, Cl, or $NO_2$. In one embodiment, $X^2$ is F, Cl, or $NO_2$. In one embodiment, $X^2$ is F or Cl. Preferably, $X^2$ is F.

$R^1$ in the occurrences herein is selected from linear or branched $C_{1-12}$ alkyl, linear or branched $C_{1-12}$ fluoroalkyl, $C_{3-8}$ cycloalkyl, linear or branched $C_{2-12}$ hydroxyalkyl, linear or branched $C_{1-12}$ carboxyalkly, phenyl and optionally substituted carboxy phenyl. In one embodiment, $R^1$ is selected from linear or branched $C_{1-12}$ alkyl, linear or branched $C_{1-12}$ fluoroalkyl, $C_{3-8}$ cycloalkyl, and phenyl. In one embodiment, $R^1$ is selected from linear or branched $C_{1-6}$ alkyl, linear or branched $C_{1-6}$ fluoroalkyl, $C_{3-8}$ cycloalkyl, linear or branched $C_{2-6}$ hydroxyalkyl, linear or branched $C_{1-6}$ carboxyalkly, phenyl and optionally substituted carboxy phenyl. For example, the carboxy phenyl may be substituted with one or more of a $C_{1-6}$ alkyl, a $C_{1-6}$ hydroxyalkyl, or a carboxy group. In one embodiment, $R^1$ is selected from linear or branched $C_{1-6}$ alkyl, linear or branched $C_{1-6}$ fluoroalkyl, $C_{3-8}$ cycloalkyl, and phenyl. In one embodiment, $R^1$ is a linear or branched $C_{1-6}$ alkyl or a $C_{3-8}$ cycloalkyl. In one embodiment, $R^1$ is a linear or branched $C_{1-6}$ alkyl. In one embodiment, $R^1$ is a linear or branched $C_{1-4}$ alkyl. Preferably, $R^1$ is selected from methyl, ethyl, n-propyl and isopropyl. More preferably, $R^1$ is methyl.

$R^{1a}$ in the occurrences herein is selected from linear or branched $C_{1-12}$ alkyl, linear or branched $C_{1-12}$ fluoroalkyl, $C_{3-8}$ cycloalkyl, and phenyl. In one embodiment, $R^{1a}$ is selected from linear or branched $C_{1-6}$ alkyl, linear or branched $C_{1-6}$ fluoroalkyl, $C_{3-8}$ cycloalkyl, and phenyl. In one embodiment, $R^{1a}$ is a linear or branched $C_{1-6}$ alkyl or a $C_{3-8}$ cycloalkyl. In one embodiment, $R^{1a}$ is a linear or branched $C_{1-6}$ alkyl. $R^{1a}$ is a linear or branched $C_{1-4}$ alkyl. Preferably, $R^{1a}$ is selected from methyl, ethyl, n-propyl and isopropyl. More preferably, $R^{1a}$ is methyl.

The optionally substituted carboxy phenyl may be substituted or unsubstituted. In one embodiment, the carboxy phenyl is unsubstituted. In one embodiment, the carboxy phenyl is substituted with a carboxylic anhydride, a carboxy group, and/or a carbonyl group.

In the processes according to the present invention, an anhydride $R^{1a}$—C(=O)OC(=O)—$R^{1a}$ (V), a cyclic anhydride or a lactone is used in the reaction with the compound of formula (III). The inventors surprisingly found, that the use of an anhydride according to formula (V), a cyclic anhydride or a lactone enables the reaction in step (i) to proceed without the use of a catalyst, particularly a copper catalyst such as a Cu(I) catalyst. Thus, with the use of an anhydride $R^{1a}$—C(=O)OC(=O)—$R^{1a}$ (V), a cyclic anhydride or a lactone in reaction step (i), the compound of formula (II) can be obtained in satisfactory yields and selectivity without the use of a catalyst, particularly a copper catalyst such as a Cu(I) catalyst. Such catalysts are usually needed when an acyl halide such as acetyl chloride is used instead of the anhydride according to formula (V), a cyclic anhydride or a lactone.

The inventors further surprisingly found that the use of an anhydride $R^{1a}$—C(=O)OC(=O)—$R^{1a}$ (V), a cyclic anhydride or a lactone in reaction step (i) to obtain the compound of formula (II) provides reduced formation of side products in the reaction.

Moreover, the use of an anhydride $R^{1a}$—C(=O)OC(=O)—$R^{1a}$ (V), a cyclic anhydride or a lactone unexpectedly reduces the work-up and recycling processes which may follow after reaction step (i). In particular, solvent separation after reaction step (i) is facilitated when using an anhydride $R^{1a}$—C(=O)OC(=O)—$R^{1a}$ (V), a cyclic anhydride or a lactone in the process for obtaining the compound of formula (II).

In one embodiment, the compound of formula (V) is selected from the group consisting of acetic anhydride, trifluoracetic anhydride, propanoic anhydride, butyric anhydride, isobutyric anhydride, trimethylacetic anhydride, benzoic anhydride and cyclopropanecarboxylic acid anhydride. Preferably, the compound of formula (V) is acetic anhydride.

In one embodiment, the cyclic anhydride used in reaction step (i) has the formula $C_nH_{2n}(CO)_2O$ wherein n is an integer from 1 to 12 (i.e. 1, 2, 3, 4, 5, 6, 7, 8, 9, 10, 11, or 12). In one embodiment, n is an integer from 1 to 6 such as 1, 2, 3, 4, 5, or 6. In one embodiment, the cyclic anhydride is selected from the group consisting of malonic anhydride, succinic anhydride, $C_1$-$C_{12}$ alkyl succinic anhydride, $C_1$-$C_{12}$ alkenyl succinic anhydride, bromo succinic anhydride, chloro succinic anhydride, glutaric anhydride, adipic anhydride, pimelic anhydride, suberic anhydride, maleic anhydride, tartaric anhydride, O-acetyl malic anhydride, diacetyl tartaric anhydride, tetrahydrophthalic anhydride, phthalic anhydride, pyromellitic dianhydride, benzene-1,2,3,4-tetracarboxylic dianhydride and methylsuccinic anhydride.

In one embodiment, the cyclic anhydride used in reaction step (i) may be further substituted. Suitable substituents include hydroxy, linear or branched $C_{1-12}$ alkyl, $C_{3-8}$ cycloalkyl, a carboxy group, halogen, and phenyl.

In one embodiment, a phenyl ring may be fused to the cyclic anhydride used in reaction step (i) including for example phthalic anhydride, pyromellitic dianhydride (benzene-1,2,4,5-tetracarboxylic dianhydride), and benzene-1,2,3,4-tetracarboxylic dianhydride.

In one embodiment the cyclic anhydride is selected from an anhydride having the formula $C_nH_m(CO)_2O$, maleic anhydride, tartaric anhydride, O-acetyl malic anhydride, diacetyl tartaric anhydride, tetrahydrophthalic anhydride, phthalic anhydride, pyromellitic dianhydride (benzene-1,2,4,5-tetracarboxylic dianhydride), and benzene-1,2,3,4-tetracarboxylic dianhydride, wherein n is an integer from 1 to 12, preferably wherein n is an integer from 1 to 6.

In one embodiment, the lactone used in reaction step (i) has the formula $C_nH_{2n}(CO)O$ wherein n is an integer from 2 to 12 (i.e. 2, 3, 4, 5, 6, 7, 8, 9, 10, 11, or 12). In one embodiment, n is an integer from 2 to 6 such as 2, 3, 4, 5, or 6. In one embodiment, the lactone is selected from the group consisting of β-lactones, γ-lactones, δ-lactones, and ε-lactones. In one embodiment, the lactone is selected from the group consisting of propiolactone, α-propiolactone, γ-butyrolactone, valerolactone, caprolactone, heptanolactone, 3,6-dimethyloxan-2-one, diketene, 4,4-dimethyloxetan-2-one, β-butyrolacton, 5-oxaspiro[2.4]heptan-6-on, 5-thiaspiro[2.4]heptan-6-on, and 4,6-dimethyloxan-2-one.

In one embodiment, the lactone used in reaction step (i) may be further substituted. Suitable substituents include hydroxy, linear or branched $C_{1-12}$ alkyl, $C_{3-8}$ cycloalkyl, a carboxy group, halogen, and phenyl.

In one embodiment, the compound of formula (V), the cyclic anhydride or the lactone is used in an amount of 0.9 eq to 1.3 eq, such as 0.97 eq to 1.3 eq or 1.0 eq to 1.3 eq, in relation to one equivalent of compound (III).

In one embodiment, the compound of formula (III) is reacted with a compound of formula (IV) and a compound according to formula (V), a cyclic anhydride or a lactone.

$R^2$ in the occurrences herein is selected from a linear or branched $C_{1-6}$ alkyl, $C_{3-6}$ cycloalkyl, and phenyl. In one embodiment, $R^2$ is selected from the group consisting of methyl, ethyl, isopropyl, tert-butyl, sec-butyl and cyclopropyl and phenyl. In one embodiment, $R^2$ is a linear or branched $C_{1-4}$ alkyl. Preferably, $R^2$ is isopropyl.

Hal in the occurrences herein is selected from fluorine, chlorine, bromine and iodine. Preferably, Hal is selected from Br and Cl. More preferably, Hal is Br.

In one embodiment, the compound of formula (IV) is selected from isopropylmagnesium bromide and isopropylmagnesium chloride. Also a combination of compounds of formula (IV) is contemplated for the processes of the present invention. For example a combination of isopropylmagnesium bromide and isopropylmagnesium chloride can be used for the processes of the present invention. Preferably, the compound of formula (IV) is isopropylmagnesium bromide.

In one embodiment, the compound of formula (IV) is used in an amount of 0.3 eq to 1.3 eq in relation to one equivalent of compound (III).

In a further embodiment, the compound of formula (III) is reacted with Mg and a compound according to formula (V), a cyclic anhydride or a lactone.

In one embodiment, Mg is used in an amount of 0.3 eq to 1.3 eq in relation to one equivalent of compound (III).

The reaction step (i) according to the present invention may be carried out in that the compound of formula (III) is first reacted with the compound of formula (IV) or Mg and subsequently, this reaction mixture is reacted with the compound of formula (V), the cyclic anhydride or the lactone. In one embodiment, the compound of formula (IV) is first reacted with the compound of formula (III) to form a Grignard reagent, which is subsequently reacted with the compound of formula (V), the cyclic anhydride or the lactone. In another embodiment, Mg is first reacted with the compound of formula (III) to form a Grignard reagent, which is subsequently reacted with the compound of formula (V), the cyclic anhydride or the lactone.

Preferably, a compound of formula (IV) is used in reaction step (i).

In one embodiment, the reaction step (i) is carried out in an organic solvent. Suitable organic solvents that may be used in the processes of the present invention are aprotic organic solvents including THF, 2-methyltetrahydrofuran, 3-methyltetrahydrofuran, diethyl ether, dibutyl-ether, dimethoxyethane, 1,4-dioxane, or in a mixture of these solvents with toluene, hexane, alkanes, ortho-xylene, meta-xylene, para-xylene, and mixtures thereof. In one embodiment, the organic solvent comprises THF. Preferably, the organic solvent is THF. In one embodiment, the reaction step (i) is carried out in THF. In one embodiment, the organic solvent used in reaction step (i) consists of THF or a mixture of THF and toluene.

In one embodiment, the process for the preparation of a compound of formula (II) is a continuous process.

In one embodiment, the compound of formula (II) is

[Structure: 4-fluoro-2-(trifluoromethyl)acetophenone]

A further subject of the present invention is a process for the preparation of a compound of formula (I)

[Structure of formula (I)]

(I)

$X^1$ is selected from H, F, $CH_3$, $CH_2F$, $CHF_2$, and $CF_3$,
$X^3$ is selected from H, F, $CH_3$, $CH_2F$, $CHF_2$, and $CF_3$,
$R^1$ is selected from linear or branched $C_{1-12}$ alkyl, $C_{1-12}$ fluoroalkyl, $C_{3-8}$ cycloalkyl, linear or branched $C_{2-12}$ hydroxyalkyl, linear or branched $C_{1-12}$ carboxyalkly, phenyl and optionally substituted carboxy phenyl, and
$R^4$ is halogen;
the process comprising
(i) the process according to the present invention for obtaining a compound of formula (II) as defined herein with the proviso that in the compound of formula (II) $X^2$ is F, Cl, or $NO_2$, and
(ii) reacting the compound of formula (II) obtained in step (i) with a compound of formula (VI)

[Structure of formula (VI)]

(VI)

wherein $R^3$ is hydrogen or an alkali metal cation.

In one embodiment, the compound of formula (I) is the compound of formula of formula (Ia)

[Structure of formula (Ia)]

(Ia)

In one embodiment, the alkali metal cation is selected from $Li^+$, $Na^+$ and $K^+$. Preferably, the alkali metal cation is Na*.

$R^4$ in the occurrences herein is halogen. In one embodiment, $R^4$ is Br or Cl. Preferably, $R^4$ is Cl.

In one embodiment, the present invention provides a process for the preparation of a compound of formula (Ia)

[Structure of formula (Ia)]

(Ia)

wherein $R^1$ is a linear or branched $C_{1-6}$ alkyl or $C_{3-8}$ cycloalkyl, and
$R^4$ is halogen;
the process comprising
(i) the process according to the present invention to obtain a compound of formula (IIa) as defined herein with the proviso that in the compound of formula (IIa) $X^2$ is F, Cl, or $NO_2$, and
(ii) reacting the compound of formula (IIa) obtained in step (i) with a compound of formula (VI)

[Structure of formula (VI)]

(VI)

wherein $R^3$ is hydrogen or an alkali metal cation.

In one embodiment, the compound of formula (I) is

[Structure with Cl, CF3]

It will be obvious for a person skilled in the art that these embodiments and items only depict examples of a plurality of possibilities. Hence, the embodiments shown here should not be understood to form a limitation of these features and configurations. Any possible combination and configuration of the described features can be chosen according to the scope of the invention.

Preferred embodiments of the present invention are further defined in the following numbered items:

1. A process for the preparation of a compound of formula (IIa)

(IIa)

wherein
X² is H, F, Cl, or NO₂, preferably F, Cl, or NO₂, and
R¹ is a linear or branched $C_{1-6}$ alkyl or $C_{3-8}$ cycloalkyl;
the process comprising
(i) reacting a compound of formula (IIIa)

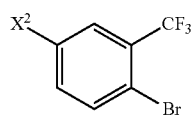

(IIIa)

with
a compound of formula (IV) R²—Mg-Hal (IV) or Mg, and
a compound of formula (V) Ria-C(=O)OC(=O)—R¹ᵃ (V), wherein
R¹ᵃ is a linear or branched $C_{1-6}$ alkyl or $C_{3-8}$ cycloalkyl
Hal is halogen, and
R² is selected from a linear or branched $C_{1-6}$ alkyl, $C_{3-6}$ cycloalkyl, and phenyl.

2. The process according to item 1, wherein in reaction step (i) no catalyst is present, preferably no copper catalyst, more preferably no Cu(I) or Cu(II) catalyst.

3. The process according to item 1 or 2, wherein in reaction step (i) no Cu(I) catalyst, preferably no CuCl catalyst, is present.

4. The process according to any one of items 1 to 3, wherein R¹ is a linear or branched $C_{1-6}$ alkyl, preferably wherein R¹ is methyl.

5. The process according to any one of items 1 to 4, wherein the compound of formula (V) is selected from the group consisting of acetic anhydride, propanoic anhydride, isobutyric anhydride, and cyclopropanecarboxylic acid anhydride, preferably wherein the compound of formula (V) is acetic anhydride.

6. The process according to any one of items 1 to 5, wherein R² is selected from the group consisting of methyl, ethyl, isopropyl, tert-butyl, sec-butyl and cyclopropyl and phenyl, preferably
wherein R² is isopropyl.

7. The process according to any one of items 1 to 6, wherein Hal is selected from Br and Cl, preferably Br.

8. The process according to any one of items 1 to 7, wherein the compound of formula (IV) is selected from isopropylmagnesium bromide, isopropylmagnesium chloride and combinations thereof, preferably wherein the compound of formula (IV) is isopropylmagnesium bromide.

9. The process according to any one of items 1 to 8, wherein reaction step (i) is carried out in an organic solvent.

10. The process according to item 9, wherein the organic solvent is THF.

11. The process according to any one of items 1 to 10, wherein the process is a continuous process.

12. The process according to any one of items 1 to 11, wherein the compound of formula (IIa) is

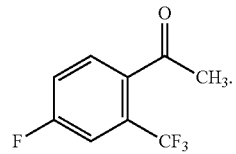

13. A process for the preparation of a compound of formula (Ia)

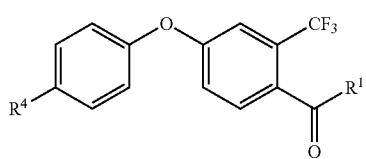

(Ia)

wherein R¹ is defined as in any one of the preceding items, and
R⁴ is halogen;
the process comprising
(i) the process according to any one of items 1 to 12 to obtain a compound of formula (IIa) as defined in any one of the preceding items, and
(ii) reacting the compound of formula (IIa) obtained in step (i) with a compound of formula (VI)

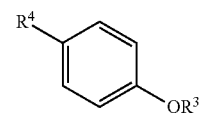

(VI)

wherein R³ is hydrogen or an alkali metal cation.

14. The process according to item 13, wherein R⁴ is Br or Cl, preferably Cl.

15. The process according to item 13 or 14, wherein the compound of formula (Ia) is

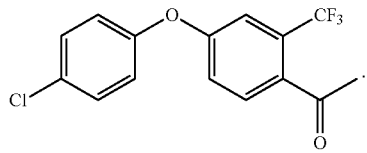

The present invention will be further illustrated by the following examples.

EXAMPLES

Example 1

63.4 g (0.26 mol, 1.00 eq) 2-bromo-5-fluorobenzotrifluoride (BFBTF) was charged into a 500 mL reactor. 197 g of a 1.18 molar (1.0 eq) iso-propyl-magnesium bromide solution in THF were added at 30° C. over 3 h. The formed BFBTF-Grignard solution was added by parallel dosage of 30.4 g acetic anhydride to a mixture of 47 g THF and 1.6 g of acetic anhydride at a temperature between −10° C. to 10° C. (total amount acetic anhydride: 0.31 mol, 1.2 eq) over 3 h.

The solvent was removed by distillation and the residue was extracted with water. The final product was isolated by distillation in a yield of 90% and purity >95% (wt % by 1H-, 19F-NMR; a % GC).

Example 2

63.4 g (0.26 mol, 1.00 eq) BFBTF was charged into a 500 mL reactor. 227 g of a 1.18 molar (1.15 eq) iso-propyl-magnesium bromide solution in THF was added at 30° C. over 3 h. The formed BFBTF-Grignard solution was added by parallel dosage of 30.4 g acetic anhydride to a mixture of 47 g THF and 1.6 g of acetic anhydride at a temperature between −10° C. to 10° C. (total amount acetic anhydride: 0.31 mol, 1.2 eq) over 3 h.

The solvent was removed by distillation and the residue was extracted with water. The final product was isolated by distillation in a yield of 90% and purity >95% (wt % by 1H-, 19F-NMR; a % GC).

Example 3

63.4 g (0.26 mol, 1.00 eq) BFBTF was charged into a 500 mL reactor. 227 g of a 1.18 molar (1.15 eq) iso-propyl-magnesium bromide solution in THF was added at 30° C. over 3 h. The formed BFBTF-Grignard solution was added by parallel dosage of 30.4 g acetic anhydride to a mixture of 47 g toluene and 1.6 g of acetic anhydride at a temperature between −10° C. to 10° C. (total amount acetic anhydride: 0.31 mol, 1.2 eq) over 3 h.

The solvent was removed by distillation and the residue was extracted with water. The final product was isolated by distillation in a yield of 90% and purity >95% (wt % by 1H-, 19F-NMR; a % GC).

Example 4

Into a 500 mL reactor, 160 g THF and 4.86 g (0.2 mol, 1 eq) Mg turnings were charged and heated to 50° C. A total of 147 g (0.6 mol, 3 eq) BFBTF was added over 2 h and allowed to stir until all Mg was dissolved. The formed Grignard solution was added by parallel dosage of 23.27 g acetic anhydride to a mixture of 36 g THF and 1.22 g of acetic anhydride at a temperature between −10° C. to 10° C. (total amount acetic anhydride: 0.24 mol, 1.2 eq) over 3 h.

The solvent was removed by distillation and the residue was extracted with water. The final product was isolated by distillation in a yield of 90% and purity >95% (wt % by 1H-, 19F-NMR; a % GC).

Example 5

Into a 500 mL reactor, 160 g THF and 4.86 g (0.2 mol, 1 eq) Mg turnings were charged and heated to 50° C. A total of 48.6 g (0.2 mol, 1 eq) BFBTF was added over 2 h and allowed to stir until all Mg was dissolved. The formed Grignard solution was added by parallel dosage of 23.27 g acetic anhydride to a mixture of 36 g THF and 1.22 g of acetic anhydride at a temperature between −10° C. to 10° C. (total amount acetic anhydride: 0.24 mol, 1.2 eq) over 3 h.

The solvent was removed by distillation and the residue was extracted with water. The final product was isolated by distillation in a yield of 90% and purity >95% (wt % by 1H-, 19F-NMR; a % GC).

Example 6

Into a 500 mL reactor, 247 g THF and 7.50 g (0.31 mol, 1 eq) Mg turnings were charged and heated to 50° C. A total of 75.0 g (0.31 mol, 1 eq) BFBTF was added over 2 h and allowed to stir until all Mg was dissolved. 55.62 g THF was added to the formed Grignard solution and 33.07 g (0.32 mol, 1.05 eq.) acetic anhydride was dosed at a temperature between −10° C. to 10° C. over 3 h.

The solvent was removed by distillation and the residue was extracted with water. The final product was isolated by distillation in a yield of 91% and purity >95% (wt % by 1H-, 19F-NMR; a % GC).

Example 7

Into a 2 L reactor, 988 g THF and 30.0 g (1.23 mol, 1 eq) Mg turnings were charged and heated to 50° C. A total of 299.9 g (1.23 mol, 1 eq) BFBTF is added over 2 h and allowed to stir until all Mg is dissolved. 126.0 g (1.23 mol, 1.0 eq.) acetic anhydride is dosed to the formed Grignard solution at a temperature between −10° C. to 10° C. over 3 h.

The solvent was removed by distillation and the residue was extracted with water. The final product was isolated by distillation in a yield of 91% and purity >95% (wt % by 1H-, 19F-NMR; a % GC).

Example 8

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 59.3 g (0.28 mol, 0.97 eq.) trifluoroacetic anhydride was dosed to the formed Grignard solution at a temperature between −10° C. to 10° C. over 3 h.

The solvent was removed by distillation and the residue was extracted with water. The final product was isolated by column chromatography (silica gel, n-hexane/ethyl acetate 100/2 v/v %) in a yield of 73% and purity >95% (wt % by 1H-, 19F-NMR; a % GC).

Example 9

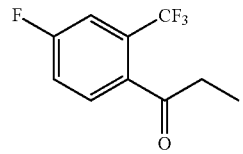

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg is dissolved. 38.2 g (0.29 mol, 1.0 eq.) propanoic anhydride was dosed to the formed Grignard solution at a temperature between −10° C. to 10° C. over 3 h.

The solvent was removed by distillation and the residue was extracted with water. The final product was isolated by column chromatography (silica gel, n-hexane/ethyl acetate 100/2 v/v %) in a yield of 89% and purity >95% (wt % by 1H-, 19F-NMR; a % GC).

Example 10

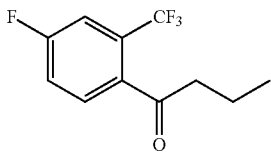 [SMILES: CCCC(=O)c1ccc(F)cc1C(F)(F)F]

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 64.5 g (0.29 mol, 1.0 eq.) butyric anhydride was dosed to the formed Grignard solution at a temperature between −10° C. to 10° C. over 3 h.

The solvent was removed by distillation and the residue was extracted with water. The final product was isolated by column chromatography (silica gel, n-hexane/ethyl acetate 100/2 v/v %) in a yield of 85% and purity >95% (wt % by 1H-, 19F-NMR; a % GC).

Example 11

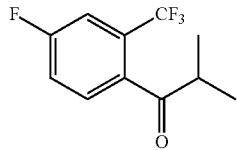

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 45.6 g (0.28 mol, 0.97 eq.) isobutyric anhydride was dosed to the formed Grignard solution at a temperature between −10° C. to 10° C. over 3 h.

The solvent was removed by distillation and the residue was extracted with water. The final product was isolated by column chromatography (silica gel, n-hexane/ethyl acetate 100/2 v/v %) in a yield of 99% and purity >95% (wt % by 1H-, 19F-NMR; a % GC).

Example 12

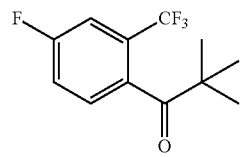 [SMILES: CC(C)(C)C(=O)c1ccc(F)cc1C(F)(F)F]

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 52.5 g (0.28 mol, 0.97 eq.) trimethylacetic anhydride was dosed to the formed Grignard solution at a temperature between −10° C. to 10° C. over 3 h.

The solvent was removed by distillation and the residue was extracted with water. The final product was isolated by column chromatography (silica gel, n-hexane/ethyl acetate 100/2 v/v %) in a yield of 84% and purity >95% (wt % by 1H-, 19F-NMR; a % GC).

Example 13

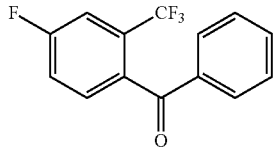 [SMILES: O=C(c1ccccc1)c1ccc(F)cc1C(F)(F)F]

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 64.5 g (0.28 mol, 0.97 eq.) benzoic anhydride was dosed to the formed Grignard solution at a temperature between −10° C. to 10° C. over 3 h.

The solvent was removed by distillation and the residue was extracted with water. The final product was isolated by column chromatography (silica gel, n-hexane/ethyl acetate 100/2 v/v %) in a yield of 98% and purity >95% (wt % by 1H-, 19F-NMR; a % GC).

Example 14

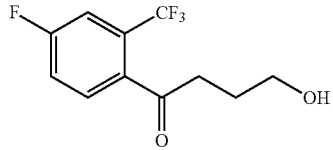

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 24.3 g (0.28 mol, 0.97 eq.) γ-butyro lactone was dosed to the formed Grignard solution at a temperature of 50° C. over 3 h.

The solvent was removed by distillation and the residue was extracted with water. The final product was isolated in a yield of 41% and purity >95% (wt % by 1H-, 19F-NMR; a % GC).

Example 15

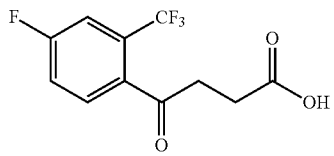 [SMILES: O=C(O)CCC(=O)c1ccc(F)cc1C(F)(F)F]

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 28.2 g (0.28 mol, 0.97 eq.) succinic anhydride was dosed to the formed Grignard solution at a temperature between −10° C. to 10° C. over 3 h.

The solvent was removed by distillation and the residue was extracted with water. The final product was isolated by column chromatography (silica gel, methylene chloride/methanol 100/2.5 v/v %) in a yield of 43% and purity >95% (wt % by 1H-, 19F-NMR; a % GC).

Example 16

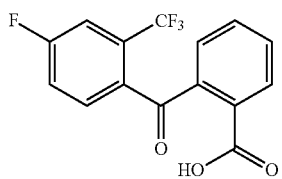 [SMILES: O=C(O)c1ccccc1C(=O)c1ccc(F)cc1C(F)(F)F]

Into a 500 mL reactor, 230 g THF and 7.00 g (0.29 mol, 1 eq) Mg turnings were charged and heated to 50° C. A total of 72.1 g (0.29 mol, 1 eq) BFBTF was added over 2 h and allowed to stir until all Mg was dissolved. 41.8 g (0.28 mol, 0.97 eq.) phthalic anhydride was dosed to the formed Grignard solution at a temperature between −10° C. to 10° C. over 3 h.

The solvent was removed by distillation and the residue was extracted with water. The final product was isolated by precipitation by the addition of diethyl ether and subsequent washing with diethyl ether and n-hexane in a yield of 88% and purity >95% (wt % by 1H-, 19F-NMR; a % GC).

Example 17

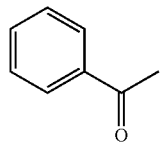

Into a 500 mL reactor, 230 g THF and 7.00 g (0.29 mol, 1 eq) Mg turnings were charged and heated to 50° C. A total of 45.7 g (0.29 mol, 1 eq) Bromobenzene was added over 2 h and allowed to stir until all Mg was dissolved. The formed Grignard solution was added by parallel dosage of 27.4 g acetic anhydride to a mixture of 80 g THF and 1.4 g of acetic anhydride at a temperature between −10° C. to 10° C. (total amount acetic anhydride: 0.28 mol, 0.98 eq) over 3 h.

The solvent was removed by distillation and the residue was extracted with water. The final product was isolated by distillation in a yield of 86% and purity >95% (wt % by 1H-, 19F-NMR; a % GC).

Example 18

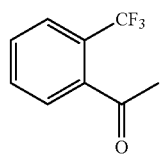

Into a 500 mL reactor, 230 g THF and 7.00 g (0.29 mol, 1 eq) Mg turnings were charged and heated to 50° C. A total of 72.1 g (0.29 mol, 1 eq) 2-bromobenzotrifluoride was added over 2 h and allowed to stir until all Mg was dissolved. 28.5 g (0.28 mol, 0.97 eq.) acetic anhydride was dosed to the formed Grignard solution at a temperature between −10° C. to 10° C. over 3 h.

The solvent was removed by distillation and the residue was extracted with water. The final product was isolated by distillation in a yield of 86% and purity >95% (wt % by 1H-, 19F-NMR; a % GC).

Example 19

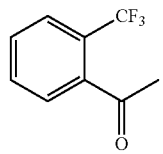

Into a 500 mL reactor, 82.3 g THF and 7.50 g (0.31 mol, 1 eq) Mg turnings were charged and heated to 50° C. 2.96 g 2-bromopropane (0.02 mol, 0.08 eq.) and a total of 55.7 g (0.31 mol, 1 eq) 2-chlorobenzotrifluoride in 165 g THF was added over 2 h and allowed to stir until all Mg was dissolved. 30.6 g (0.30 mol, 0.97 eq.) acetic anhydride was dosed to the formed Grignard solution at a temperature between −10° C. to 10° C. over 3 h.

The solvent was removed by distillation and the residue was extracted with water. The final product was isolated by distillation in a yield of 71% and purity >95% (wt % by 1H-, 19F-NMR; a % GC).

Example 20

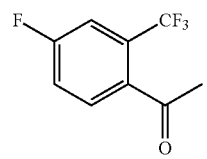

Into a 500 mL reactor, 64.1 g THF and 5.85 g (0.24 mol, 1 eq) Mg turnings were charged and heated to 50° C. 2.27 g 2-bromopropane (0.02 mol, 0.08 eq.) and a total of 50.2 g (0.24 mol, 1 eq) 2-chloro-5-fluorobenzotrifluoride in 128 g THF was added over 2 h and allowed to stir until all Mg was dissolved. 23.8 g (0.23 mol, 0.97 eq.) acetic anhydride was dosed to the formed Grignard solution at a temperature between −10° C. to 10° C. over 3 h.

The solvent was removed by distillation and the residue was extracted with water. The final product was isolated by distillation in a yield of 12% and purity >95% (wt % by 1H-, 19F-NMR; a % GC).

Example 21

Into a 500 mL reactor, 230 g THF and 7.00 g (0.29 mol, 1 eq) Mg turnings were charged and heated to 50° C. A total of 61.4 g (0.29 mol, 1 eq) 2-Bromo-1,3,5-trifluorobenzene was added over 2 h and allowed to stir until all Mg was dissolved. 28.5 g (0.28 mol, 0.97 eq.) acetic anhydride was dosed to the formed Grignard solution at a temperature between −10° C. to 10° C. over 3 h.

The solvent was removed by distillation and the residue was extracted with water. The final product was isolated by distillation in a yield of 60% and purity >95% (wt % by 1H-, 19F-NMR; a % GC).

What is claimed:
1. A process for the preparation of a compound of formula (II)

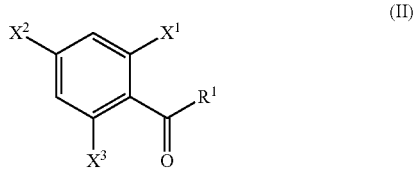

wherein
$X^1$ is selected from F, $CH_2F$, $CHF_2$, and $CF_3$,
$X^2$ is H, F, Cl, or $NO_2$,
$X^3$ is selected from H, F, $CH_3$, $CH_2F$, $CHF_2$, and $CF_3$, and
$R^1$ is selected from linear or branched $C_{1-12}$ alkyl, linear or branched $C_{1-12}$ fluoroalkyl, $C_{3-8}$ cycloalkyl, linear or branched $C_{2-12}$ hydroxyalkyl, linear or branched $C_{1-12}$ carboxyalkly, phenyl and optionally substituted carboxy phenyl;
the process comprising
(i) reacting a compound of formula (III)

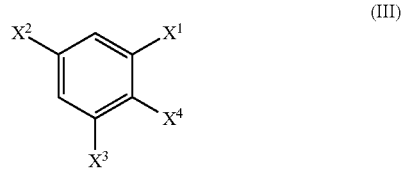

wherein $X^4$ is Br or Cl
with
a compound of formula (IV) $R^2$—Mg-Hal (IV) or Mg, and a compound of formula (V) $R^{1a}$—C(=O)OC(=O)—$R^{1a}$ (V), a cyclic anhydride or a lactone,
wherein
$R^{1a}$ is selected from linear or branched $C_{1-12}$ alkyl, linear or branched $C_{1-12}$ fluoroalkyl, $C_{3-8}$ cycloalkyl, and phenyl,
Hal is halogen, and
$R^2$ is selected from a linear or branched $C_{1-6}$ alkyl, $C_{3-6}$ cycloalkyl, and phenyl wherein in reaction step (i) no catalyst is present.

2. The process according to claim 1, wherein in reaction step (i) no Cu(I) catalyst is present.

3. The process according to claim 1, wherein $R^1$ is selected from a group consisting of linear or branched $C_{1-6}$ alkyl, linear or branched $C_{1-6}$ fluoroalkyl, $C_{3-8}$ cycloalkyl, linear or branched $C_{2-6}$ hydroxyalkyl, linear or branched $C_{1-6}$ carboxyalkly, phenyl and optionally substituted carboxy phenyl.

4. The process according to claim 1, wherein $R^{1a}$ is selected from a group consisting of linear or branched $C_{1-6}$ alkyl, linear or branched $C_{1-6}$ fluoroalkyl, $C_{3-8}$ cycloalkyl, and phenyl.

5. The process according to claim 1, wherein the compound of formula (V) is selected from the group consisting of acetic anhydride, trifluoroacetic anhydride, propanoic anhydride, butyric anhydride, isobutyric anhydride, trimethylacetic anhydride, benzoic anhydride, and cyclopropanecarboxylic acid anhydride.

6. The process according to claim 1, wherein the cyclic anhydride is selected from the group consisting of maleic anhydride, tartaric anhydride, O-acetyl malic anhydride, diacetyl tartaric anhydride, tetrahydrophthalic anhydride, phthalic anhydride, pyromellitic dianhydride, benzene-1,2,3,4-tetracarboxylic dianhydride, and an anhydride having the formula $C_nH_{2n}(CO)_2O$ wherein n is an integer from 1 to 12.

7. The process according to claim 1, wherein the cyclic anhydride is selected from the group consisting of malonic anhydride, succinic anhydride, $C_1$-$C_{12}$ alkyl succinic anhydride, $C_1$-$C_{12}$ alkenyl succinic anhydride, bromo succinic anhydride, chloro succinic anhydride, glutaric anhydride, adipic anhydride, pimelic anhydride, suberic anhydride, methylsuccinic anhydride, maleic anhydride, tartaric anhydride, O-acetyl malic anhydride, diacetyl tartaric anhydride, tetrahydrophthalic anhydride, phthalic anhydride, pyromellitic dianhydride (benzene-1,2,4,5-tetracarboxylic dianhydride), and benzene-1,2,3,4-tetracarboxylic dianhydride.

8. The process according to claim 1, wherein the lactone has the formula $C_nH_{2n}(CO)O$ wherein n is an integer from 2 to 12.

9. The process according to claim 1, wherein the lactone used in reaction step (i) is selected from the group consisting of β-lactones, γ-lactones, δ-lactones, and ε-lactones.

10. The process according to claim 1, wherein the compound of formula (II) is the compound of formula (IIa)

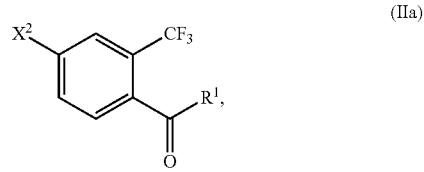

and
wherein the compound of formula (III) is the compound of formula (IIIa)

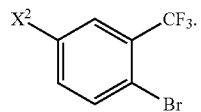
(IIIa)

11. The process according to claim 1, wherein $X^2$ is F, Cl, or $NO_2$.

12. The process according to claim 1, wherein $R^2$ is selected from the group consisting of methyl, ethyl, isopropyl, tert-butyl, sec-butyl and cyclopropyl, and phenyl.

13. The process according to claim 1, wherein Hal is selected from Br and Cl.

14. The process according to claim 1, wherein the compound of formula (IV) is selected from isopropylmagnesium bromide, isopropylmagnesium chloride, and combinations thereof.

15. The process according to claim 1, wherein reaction step (i) is carried out in an organic solvent.

16. The process according to claim 15, wherein the organic solvent is THF.

17. The process according to claim 1, wherein the process is a continuous process.

18. The process according to claim 1, wherein the compound of formula (II) is

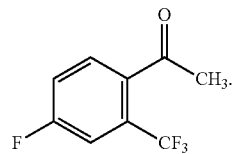

19. A process for the preparation of a compound of formula (I)

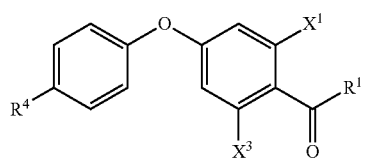
(I)

wherein $R^1$, $X^1$ and $X^3$ are defined as in claim 1, and
$R^4$ is halogen;
the process comprising:
(i) the process according to claim 1 to obtain a compound of formula (II) as defined in claim 1 wherein in the compound of formula (II) $X^2$ is F, Cl, or $NO_2$, and
(ii) reacting the compound of formula (II) obtained in step (i) with a compound of formula (VI)

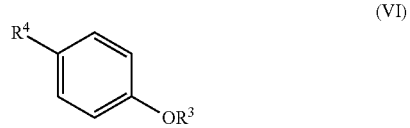
(VI)

wherein $R^3$ is hydrogen or an alkali metal cation.

20. The process according to claim 19, wherein the compound of formula (I) is the compound of formula of formula (Ia)

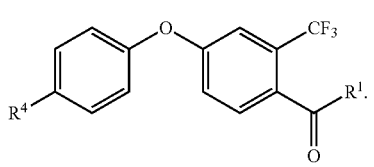
(Ia)

21. The process according to claim 19, wherein $R^4$ is Br or Cl.

22. The process according to claim 19, wherein the compound of formula (I) is

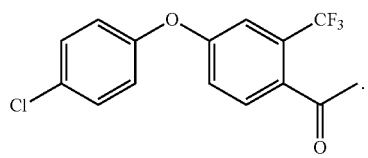 [SMILES: CC(=O)c1ccc(Oc2ccc(Cl)cc2)cc1C(F)(F)F]

* * * * *